United States Patent [19]

Takatori et al.

[11] 4,335,247
[45] Jun. 15, 1982

[54] NOVEL NITROSOUREA DERIVATIVES AND PROCESS FOR THEIR PRODUCTION

[75] Inventors: Kichitaro Takatori, Nagoya; Takashi Yamaguchi, Urawa; Masahiko Nagakura, Sayama, all of Japan

[73] Assignee: Kowa Co., Ltd., Nagoya, Japan

[21] Appl. No.: 237,273

[22] Filed: Feb. 23, 1981

[30] Foreign Application Priority Data

Feb. 28, 1980 [JP] Japan ................... 55-24491

[51] Int. Cl.³ ............................................ C07C 127/1
[52] U.S. Cl. ........................................ 548/140; 564/33; 568/949; 562/553; 562/597
[58] Field of Search .................... 548/140; 564/33, 37, 564/112; 568/949; 562/553, 557

[56] References Cited

U.S. PATENT DOCUMENTS

| | | | |
|---|---|---|---|
| 3,859,277 | 1/1975 | Murakami et al. | 564/33 |
| 4,028,410 | 6/1977 | Yanko et al. | 564/33 |
| 4,039,578 | 8/1977 | Suami | 564/33 |
| 4,148,921 | 4/1979 | Suami | 564/33 |
| 4,175,081 | 11/1979 | Driscoll | 548/140 |

OTHER PUBLICATIONS

*Chemical Abstract*, vol. 88, #83362k, Masahito et al., 1977.
*Chemical Abstract*, vol. 83, #58706q, Zhelyakov, 1974.
*Chemical Abstract*, vol. 81, #77156k, Lyh et al., 1974.

*Primary Examiner*—Thomas A. Waltz
*Assistant Examiner*—Raymond Covington
*Attorney, Agent, or Firm*—Oblon, Fisher, Spivak, McClelland & Maier

[57] ABSTRACT

The specification describes a nitrosourea derivative having the general formula: Cl—(CH$_2$)$_2$—N(NO)-CO—NHR, wherein —NHR represents a 2-(1,3,4-thiadiazolyl)amino group, an amino residue of a neutral α-amino acid, or an amino residue of a neutral α-amino acid whose carboxyl group is amidated with 2-(1,3,4-thiadiazolyl)amine, or a pharmaceutically acceptable acid addition salt thereof. The above nitrosourea derivative and its salt are useful as antitumor drugs. The above nitrosourea derivative may be prepared either by nitrosating a urea derivative of the general formula: Cl—(CH$_2$)$_2$NHCONHR or by reacting N-(2-chloroethyl)-N-nitrosocarbamic acid or a reactive derivative thereof with an amino compound of the general formula: R—NH$_2$.

2 Claims, No Drawings

NOVEL NITROSOUREA DERIVATIVES AND PROCESS FOR THEIR PRODUCTION

BACKGROUND OF THE INVENTION

1. Field of the Invention

The present invention relates to a novel nitrosourea derivative or a pharmaceutically acceptable acid addition salt thereof. Particularly it is concerned with a nitrosourea derivative represented by the general formula (I),

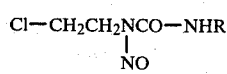
(I)

wherein —NHR represents a 2-(1,3,4-thiadiazolyl)amino group, an amino residue of a neutral α-amino acid, or an amino residue of a neutral α-amino acid whose carboxyl group is amidated with 2-(1,3,4-thiadiazolyl)amine, or a pharmaceutically acceptable acid addition salt of the derivatives, as well as also with processes for producing the same.

2. Description of the Prior Art

There have been known many N-(2-chloroethyl)-N-nitrosourea compounds which are useful as antitumor substance of alkylating agent type. On the other hand, the present inventors have previously found that a certain amide compound prepared by condensing 2-amino-1,3,4-thiadiazole with an amino acid has a strong antitumor effect as a metabolic antagonist for nicotinic acid necessary for glycolysis which is actively taken place in cancer tissues, and have applied for a patent (Japanese Patent Application No. 128146/78).

SUMMARY OF THE INVENTION

Having synthesized the compound of the general formula (I) with these functionally different groups combined, i.e. the compound obtained by combining N-(2-chloroethyl)-N-nitrosourea with said amide compound or an amino acid constituting it, or with 2-(1,3,4-thiadiazolyl)amine, and having studied its biological activities, the present inventors have found that it has a superior antitumor effect and have thus accomplished the present invention.

Thus, in one aspect of this invention, there is provided a nitrosourea derivative represented by the general formula,

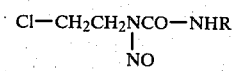

wherein —NHR represents a 2-(1,3,4-thiadiazolyl)amino group, an amino residue of a neutral α-amino acid, or an amino residue of a neutral α-amino acid whose carboxyl group is amidated with 2-(1,3,4-thiadiazolyl)amine, or a pharmaceutically acceptable acid addition salt thereof. The nitrosourea derivative and its pharmaceutically acceptable salt are useful as antitumor drugs.

In another aspect of this invention there is provided a process for producing a nitrosourea derivative represented by the general formula,

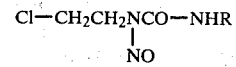

wherein —NHR represents a 2-(1,3,4-thiadiazolyl)amino group, an amino residue of a neutral α-amino acid, or an amino residue of a neutral α-amino acid whose carboxyl group is amidated with 2-(1,3,4-thiadiazolyl)amine or a pharmaceutically acceptable acid addition salt thereof, which is characterized by nitrosating a urea derivative represented by the general formula,

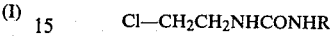

wherein —NHR is as defined above, and when the salt is desired, converting the nitrosourea to the salt by a method known per se in the art.

In a further aspect of this invention there is also provided a process for producing a nitrosourea derivative represented by the general formula,

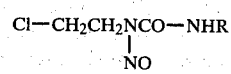

wherein —NHR represents a 2-(1,3,4-thiadiazolyl)amino group, an amino residue of a neutral α-amino acid, or an amino residue of a neutral α-amino acid whose carboxyl group is amidated with 2-(1,3,4-thiadiazolyl)amine or a pharmaceutically acceptable acid addition salt thereof, which is characterized by reacting N-(2-chloroethyl)-N-nitrosocarbamic acid or a reactive derivative thereof with an amino compound represented by the general formula R—NH$_2$ wherein —NHR is as defined above, and when the salt is desired, converting the nitrosourea to the salt by a method known per se in the art.

DETAILED DESCRIPTION OF THE INVENTION

Particularly preferred among the compounds (I) of the present invention are those having the formula (II),

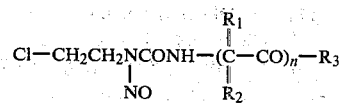

wherein R$_1$ and R$_2$ each represents a hydrogen atom, or a linear or branched lower alkyl, indolylalkyl, hydroxyalkyl, loweralkyl-thioalkyl, aryl or aralkyl group, or R$_1$ and R$_2$ combine together to form an alkylene group, n represents 0 or 1, and R$_3$ represents a 1,3,4-thiadiazol-2-yl group when n is 0, and a hydroxyl group or a 2-(1,3,4-thiadiazolyl)amino group when n is 1.

As the neutral α-amino residue represented by

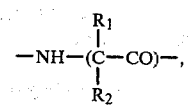

which constitutes the compounds of the formula II, there may be mentioned, for instance, the residue of glycine, alanine, valine, leucine, isoleucine, cycloleucine, phenyl glycine, phenyl alanine, serine, threonine, methionine, cysteine, proline, tyrosine, tryptophane or the like.

The compound (I) of the present invention may be prepared, for instance, by the following processes:

(1) Process 1

(II)

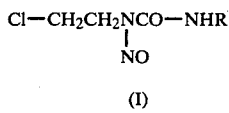

(I)

wherein —NHR is as defined above.

Namely, the nitrosourea compound (I) is prepared by nitrosating the urea derivative (II).

The urea derivative (II) as the starting material is a novel compound and may be prepared, for instance, (1) by reacting N-(2-chloroethyl)carbamic acid or its reactive derivative with an amino compound represented by the general formula R—NH$_2$ (III) where R is as defined above, or (2) by reacting N-(2-chloroethyl)carbamic acid or its reactive derivative with an amino compound represented by the general formula R$^1$—NH$_2$ (IV) wherein R$^1$ represents an amino residue of a neutral α-amino acid, and reacting the resulting product (a compound of the general formula (II) wherein —NHR is an amino residue of a neutral α-amino acid) with 2-amino-1,3,4-thiadiazole.

(2) Process 2

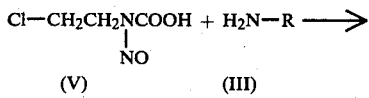

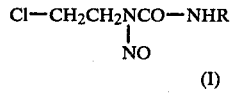

(I)

wherein —NHR is as defined above.

Namely, the nitrosourea derivative (I) is prepared by reacting N-(2-chloroethyl)-N-nitrosocarbamic acid (V) or its reactive derivative with an amino compound (III).

As the reactive derivatives of N-(2-chloroethyl)carbamic acid and N-(2-chloroethyl)-N-nitrosocarbamic acid, there may be used the corresponding chlorides, nitroamides, esters and isocyanates. Generally this condensation reaction is carried out by reacting almost the same amounts of both starting materials (III) and (V) in the presence or absence of a solvent at a temperature of from 0° to 250° C. for from 1 to 30 hours, which may vary depending upon the type of each of the starting materials actually used. As the solvent, water-dioxane, tetrahydrofuran, alcohols, acetonitrile, benzene, ether, chloroform, methylene chloride, pyridine or the like, may be used.

The nitrosation can be conducted according to a usual method, such as by reacting a metal salt of alkylester of nitrous acid in the presence of an acid, or by effectively applying a nitrosating agent such as nitrosyl chloride or nitrogen trioxide.

Further, the amino compounds (III) as the starting material may include the L-, D- and DL- isomers. According to the method of the present invention, these optical activities are not impaired.

The compound of the formula (I) thus prepared, can be converted to a pharmaceutically acceptable acid addition salt in accordance with the usual methods. As the acids to be used for the preparation of such acid addition salts, there may be mentioned, for instance, inorganic acids such as hydrochloric acid, hydrobromic acid, hydriodic acid, sulfuric acid, nitric acid, phosphoric acid and the like; and organic acids such as acetic acid, propionic acid, dichloroacetic acid, benzilic acid, salicylic acid, oxalic acid, malonic acid, adipic acid, maleic acid, fumaric acid, tartaric acid, citric acid, ascorbic acid and the like.

The compounds of the formula (I) wherein R is an amino residue of a neutral α-amino acid, can be made in a form of an alkali salt with sodium, potassium, calcium or the like.

Further, in order to improve the stability and solubility of these compounds, it is possible to convert them into inclusion compounds with cyclodextrin in accordance with the usual method.

Now, the results obtained from the tests of antitumor effects and acute toxicity with respect to some typical compounds (I) of the present invention will be shown.

(1) Test Compounds:

A. 2-{3-(2-chloroethyl)-3-nitrosoureido}-1,3,4-thiadiazole
B. N-{(2-chloroethyl)-nitrosocarbamoyl}-L-valine
C. N-{(2-chloroethyl)-nitrosocarbamoyl}-L-valine.β-cyclodextrin inclusion compound
D. 2-[N-{(2-chloroethyl)-nitrosocarbamoyl}-L-valyl]amino-1,3,4-thiadiazole
E. 2-[N-{(2-chloroethyl)-nitrosocarbamoyl}-DL-leucyl]amino-1,3,4-thiadiazole
F. 2-[N-{(2-chloroethyl)-nitrosocarbamoyl}-L-leucyl]amino-1,3,4-thiadiazole
G. 2-[N-{(2-chloroethyl)-nitrosocarbamoyl}-L-isoleucyl]amino-1,3,4-thiadiazole
H. 2-[N-{(2-chloroethyl)-nitrosocarbamoyl}-L-methionyl]amino-1,3,4-thiadiazole
I. 2-[N-{(2-chloroethyl)-nitrosocarbamoyl}-D-phenylglycyl]amino-1,3,4-thiadiazole
J. 2-[N-{(2-chloroethyl)-nitrosocarbamoyl}-L-phenylalanyl]amino-1,3,4-thiadiazole
K. 2-[1-{(2-chloroethyl)-nitrosocarbamoyl}-cycoleucyl]amino-1,3,4-thiadiazole
L. 2-[N-{(2-chloroethyl)-nitrosocarbamoyl}-DL-threonyl{amino-1,3,4-thiadiazole
M. 2-[N-{(2-chloroethyl)-nitrosocarbamoyl}-L-tryptophyl]amino-1,3,4-thiadiazole
N. 2-[N-{(2-chloroethyl)-nitrosocarbamoyl}-D-valyl]amino-1,3,4-thiadiazole
O. 2-[N{(2-chloroethyl)-nitrosocarbamoyl}-D-leucyl]amino-1,3,4-thiadiazole (2) Acute Toxicity The median lethal dose (LD$_{50}$) of each of the test compounds was determined by the Litchfield-Wilcoxon method after the intraperitoneal injection of the compound into ddy mice.

The results obtained are shown in Table 1.

TABLE 1

| Test Compound | LD$_{50}$ (mg/Kg) |
|---|---|
| A | 78 |
| B | 72 |
| C | 320 |
| D | 49 |
| E | 82 |
| F | 85 |
| G | 78 |
| H | 67 |
| I | 69 |
| J | 74 |
| K | 53 |
| L | 65 |
| M | 73 |
| N | 68 |
| O | 61 |

(3) Anti-tumor Test

Each experimental group was composed of six CDF$_1$ mice. The mice were inoculated intraperitoneally with 10$^6$ P388 cancer cell, and the test compounds suspended in a gum arabic were administered intraperitoneally to the animals 24 hours and 5 days, respectively, after the inoculation. The survival effect of each of the compounds was expressed by the percentage of the survival days of the treated animals in each group relative to those of the control animals.

The results obtained are shown in Table 2.

TABLE 2

| Test Compound | Dose (mg/Kg/day) | Survival Effect T/C(%) | Cure | Tumored Survivors |
|---|---|---|---|---|
| A | 50 | 172 | | |
|   | 25 | 173 | | |
|   | 12.5 | 170 | | |
| B | 50 | 297 | 1/6 | 1/6 |
|   | 25 | 230 | | |
| C | 200 | 230 | 1/6 | |
|   | 100 | 170 | | |
| D | 25 | 291 | 5/6 | 2.6 |
|   | 12.5 | 281 | 2.6 | |
|   | 6.25 | 223 | | |
| E | 50 | 303 | 5/6 | |
|   | 25 | 303 | 2/6 | 1/6 |
|   | 12.5 | 220 | | |
| F | 25 | 303 | 3/6 | 2/6 |
|   | 12.5 | 292 | 1/6 | 1/6 |
| G | 50 | 297 | 3/6 | 2/6 |
|   | 25 | 297 | 1/6 | 3/6 |
|   | 12.5 | 247 | 1/6 | |
| H | 50 | 294 | 5/6 | 1/6 |
|   | 25 | 294 | 3/6 | 2/6 |
|   | 12.5 | 235 | 1/6 | |
| I | 50 | 297 | 5/6 | |
|   | 25 | 297 | 2/6 | 2/6 |
|   | 12.5 | 297 | 2/6 | 1/6 |
| J | 50 | 297 | 4/6 | 1/6 |
|   | 25 | 297 | 5/6 | |
|   | 12.5 | 297 | 2/6 | 1/6 |
| K | 50 | 176 | | |
|   | 25 | 176 | | |
|   | 12.5 | 175 | | |
| L | 50 | 81 | | |
|   | 25 | 93 | 1/6 | |
|   | 12.5 | 153 | | |
| M | 100 | 107 | 1/6 | |
|   | 50 | 294 | 3/6 | 2/6 |
|   | 25 | 294 | 5/6 | |
| N | 50 | 99 | 2/6 | |
|   | 25 | 217 | 1/6 | |
| O | 100 | 188 | | |
|   | 50 | 217 | | |
|   | 25 | 190 | | |

Further, the compounds of the invention possess remarkably excellent survival effects on the mice inoculated with L1210 leukemia, Ehrlich carcinoma (solid type), Crocker sarcoma, melanoma and colon 38.

This invention will now be described in further detail with reference to certain specific Examples, which are presented herein for purposes of illustration only and are not be construed as limiting unless otherwise specified.

EXAMPLE 1

(1) Ten grams of 2-amino-1,3,4-thiadiazole was dissolved in 100 ml of a tetrahydrofuran, to which was added dropwise 50 ml of a tetrahydrofuran solution containing 11 g of N-2-chloroethyl isocyanate. The mixture was stirred for 4 hours. After the reaction, the precipitates were collected by filtration, washed with ether and dried to obtain 18.7 g (Yield 91%) of 2-{3-(2-chloroethyl)-ureido}-1,3,4-thiadiazole as colourless crystals having a melting point of 164° C. (dec.).

(2) The above condensation product in an amount of 20.7 g was dissolved in a mixed solution containing 40 ml of glacial acetic acid and 160 ml of acetic anhydride, and while cooling the solution with ice, 76 g of sodium nitrite was gradually added. The mixture was stirred at 0° C. for further 3 hours. The reaction solution was poured into ice water and the precipitated crystals were collected by filtration, washed with water, cold ethanol, and ether in this order, then dried and recrystallized from methanol, to obtain 17.2 g (Yield 73%) of 2-{3-(2-chloroethyl)-3-nitrosoureido}-1,3,4-thiadiazole as slightly yellow prisms having a melting point of 127° C. (dec.).

Elementary analysis: Calculated for $C_5H_6O_2SCl$ (%): C: 25.48; H: 2.57; N: 29.72; Found (%): C: 25.51; H: 2.53; N: 29.72.

EXAMPLE 2

Ten grams of 2-amino-1,3,4-thiadiazole, 16.6 g of 1-(2-chloroethyl)-3-nitrourea and 84 g of sodium hydrogencarbonate were stirred in 100 ml of diluted ethanol at a temperature of 80° C. for 2 hours. While being still hot after the reaction, the precipitated inorganic matters were removed by filtration, and the filtrate was cooled. The precipitated crystals were collected by filtration and washed with water, to obtain 14.7 g (Yield 71%) of 2-{3-(2-chloroethyl)ureido}-1,3,4-thiadiazole. The product was then treated in the same manner as in Example 1 (2), to obtain 2-{3-(2-chloroethyl)-3-nitrosoureido}-1,3,4-thiadiazole.

EXAMPLE 3

Ten grams of 2-amino-1,3,4-thiadiazole was dissolved in 100 ml of pyridine, and cooled with ice. While stirring the solution, 26.5 g of N-(2-chloroethyl)-N-nitrosocarbamoyl azide was gradually added, and after the addition, the stirring was continued for 60 minutes. The reaction solution was poured into ice water, and the precipitated crystals were washed with water, dried and recrystallized from methanol, to obtain 17.8 g (Yield 75%) of 2-{3-(2-chloroethyl)-3-nitrosoureido}-1,3,4-thiadiazole. The physical properties of this compound were identical with those of the compound obtained by Example 1.

EXAMPLE 4

(1) Six grams of L-valine was dissolved in a 5% aqueous potassium carbonate solution, to which was added dropwise 5.5 g of N-2-chloroethyl isocyanate while cooling with ice. The mixture was stirred for further 3 hours. The reaction solution was washed with ether, neutralized with hydrochloric acid, and extracted with ether, to obtain 8.9 g (Yield 78%) of N-{(2-chloroethyl)carbamoyl}-L-valine as a slightly yellow oil.

Specific rotation: $[\alpha]_D^{20}$ +5.7° (c 1, MeOH).

(2) 8.4 g of N-(2-chloroethyl)carbamoyl-L-valine obtained by the above process and 4.0 g of triethylamine were dissolved in 200 ml of tetrahydrofuran to which was added 4.4 g of ethyl chlorocarbonate while cooling with sodium chloride-ice. After stirring the mixture for 2 hours, 4.0 g of 2-amino-1,3,4-thiadiazole was added and stirred for further 20 hours. The reaction solution was concentrated and the precipitated crystals were collected by filtration, washed with water, and dried, to obtain 9.8 g (Yield 85%) of 2-[N-{(2-chloroethyl)carbamoyl}-L-valyl]amino-1,3,4-thiadiazole as colourless crystals having a melting point of from 177° to 180° C. (dec.).

Specific rotation: $[\alpha]_D^{20}$ −7.2° (c 1, MeOH).

(3) 9.4 g of (2-[N-{(2-chloroethyl)carbamoyl}-L-valyl]amino-1,3,4-thiadiazole obtained by the above process was suspended in a mixed solution containing 11 ml of acetic acid and 52 ml of acetic anhydride, and 25 g of sodium nitrite was gradually added thereto at 0° C. After stirring the solution for 3 hours, the reaction solution was poured into ice water and the precipitated crystals were collected by filtration. The crystals were recrystallized from ethanol, to obtain 9.4 g (Yield 91%) of 2-[N-{(2-chloroethyl)-nitrosocarbamoyl}-L-valyl]amino-1,3,4-thiadiazole as slightly yellow prisms having a melting point of 134° C. (dec.).

Elementary analysis: Calculated for $C_{10}H_5N_6O_3SCl$ (%): C: 35.88; H: 4.52; N: 25.10; Found (%): C: 36.17; H: 4.53; N: 25.01.

Specific rotation: $[\alpha]_D^{20}$ +42.3° (c 1, MeOH).

EXAMPLE 5

(1) 7.5 g of 2-DL-leucylamino-1,3,4-thiadiazole hydrochloride and 3.1 g of triethylamine were suspended in 100 ml of tetrahydrofuran, and 3.2 g of 2-chloroethyl isocyanate was added thereto and stirred for 2 hours. The reaction solution was concentrated, and the resulting crystals were washed with water and n-hexane to obtain 7.9 g (Yield 83%) of 2-[N-{(2-chloroethyl)carbamoyl}-DL-leucyl]amino-1,3,4-thiadiazole was obtained as slightly yellow crystals having a melting point of from 162° to 166° C. (dec.).

(2) In a manner similar to Example 4(3), 7.9 g of the compound obtained by the above process was treated to obtain 5.5 g (Yield 64%) of 2-[N-{(2-chloroethyl)-nitrosocarbamoyl}-DL-leucyl]amino-1,3,4-thiadiazole as slightly yellow prisms having a melting point of 147° C. (dec.).

Elementary analysis: Calculated for $C_{11}H_{17}N_6O_3SCl$ (%): C: 37.88; H: 4.91; N: 24.09; Found (%): C: 38.09; H: 4.93; N: 24.39.

EXAMPLE 6

In a manner similar to Example 4, 8.6 g of L-leucine was treated for reaction to obtain 8.7 g (Yield 38%) of 2-[N-{(2-chloroethyl)-nitrosocarbamoyl}-L-leucyl]amino-1,3,4-thiadiazole as slightly yellow prisms having a melting point of 127° C. (dec.).

Elementary analysis: Calculated for $C_{11}H_{17}N_6O_3SCl$ (%): C: 37.88; H: 4.91; N: 24.09; Found (%): C: 37.96; H: 4.92; N: 24.11.

Specific rotation: $[\alpha]_D^{20}$ +20.6° C. (c 1, MeOH).

EXAMPLE 7

In a manner similar to Example 4, 8.6 g of L-isoleucine was treated for reaction to obtain 9.6 g (Yield 42%) of 2-[N-{(2-chloroethyl)-nitrosocarbamoyl}-L-isoleucyl]amino-1,3,4-thiadiazole as slightly yellow prisms having a melting point of 119° C. (dec.).

Elementary analysis: Calculated for $C_{11}H_{17}N_6O_3SCl$ (%): C: 37.88; H, 4.91; N: 24.09; Found (%): C: 38.06; H: 4.88; N: 24.02.

Specific rotation: $[\alpha]_D^{20}$ +41.8° (c 1.1, MeOH).

EXAMPLE 8

In a manner similar to Example 4, 10.4 g of L-methionine was treated for reaction to obtain 13.1 g (Yield 51%) of 2-[N-{(2-chloroethyl)-nitrosocarbamoyl}-L-methionyl]amino-1,3,4-thiadiazole as slightly yellow prisms having a melting point of 140° C. (dec.).

Elementary analysis: Calculated for $C_{10}H_{15}N_6O_3S_2Cl$ (%): C: 32.74; H: 4.12; N: 22.91; Found (%): C: 32.99; H, 4.11; N: 22.77.

Specific rotation $[\alpha]_D^{20}$ +4.6° (c 1, MeOH).

EXAMPLE 9

In a manner similar to Example 4, 10 g of D-phenylglycine was treated for reaction to obtain 8.6 g (Yield 35%) of 2-[N-{(2-chloroethyl)-nitrosocarbamoyl}-D-phenylglycyl]amino-1,3,4-thiadiazole as slightly yellow prisms having a melting point of 154° C. (dec.).

Elementary analysis: Calculated for $C_{13}H_{13}N_6O_3SCl$ (%): C: 42.34; H: 3.55; N: 22.79; Found (%): C: 42.38; H: 3.52; N: 22.71.

Specific rotation: $[\alpha]_D^{20}$ −0.57° (c 0.18, MeOH).

EXAMPLE 10

In a manner similar to Example 4, 8.0 g of L-phenylalanine was treated for reaction to obtain 11.7 g (Yield 63%) of 2-[N-{(2-chloroethyl)-nitrosocarbamoyl}-L-phenylalanyl]amino-1,3,4-thiadiazole as slightly yellow prisms having a melting point of 130° C. (dec.).

Elementary analysis: Calculated for $C_{14}H_{15}N_6O_3SCl$ (%): C: 43.92; H: 3.95; N: 21.95; Found (%): C: 43.80; H: 3.89; N: 22.03.

Specific rotation: $[\alpha]_D^{20}$ +16.3° (c 1.1, MeOH).

EXAMPLE 11

In a manner similar to Example 5, 7.6 g of 2-cycloleucylamino-1,3,4-thiadiazole hydrochloride was treated for reaction to obtain 6.2 g (Yield 59%) of 2-[N-{(2-chloroethyl)-nitrosocarbamoyl}-cycloleucyl]amino-1,3,4-thiadiazole as slightly yellow prisms having a melting point of 160° C.

Elementary analysis: Calculated for $C_{11}H_{15}N_6O_3SCl$ (%): C: 38.10; H: 4.36; N: 24.23; Found (%): C: 38.04; H: 4.32; N: 24.12.

EXAMPLE 12

(1) Dissolved in a 5% aqueous potassium carbonate solution was 2.1 g of L-valine, and a tetrahydrofuran solution containing 3.2 g of (2-chloroethyl)-nitrosocarbamoyl azide was added at 0° C. The mixture was stirred for two hours. The reaction solution was washed with ether, neutralized with hydrochloric acid, and extracted with ether to obtain 2.9 g (Yield 64%) of N-{(2-chloroethyl)-nitrosocarbamoyl}-L-valine as a slightly yellow oil.

Specific rotation: $[\alpha]_D^{20}$ +20.0° (c 2.1 MeOH).

(2) Dissolved under heating in 480 ml of water, was 22 g of β-cyclodextrin, and an aceton solution containing 2.5 g of N-{(2-chloroethyl)-nitrosocarbamoyl}-L-valine was added thereto at a temperature of from 50° to 60° C. and then left to stand at room temperature. The precipitated crystals were collected by filtration and washed with water and ether to obtain 13.2 g (Yield 54%) of an inclusion compound as slightly yellow powder having a melting point of from 228° to 230° C. (dec.).

Elementary analysis: Calculated for $C_8H_{14}N_3O_4Cl \cdot (C_6H_{10}O_5)_7 \times 2$ (%): C: 43.81; H: 6.15; N: 1.67; Found (%): C: 43.21; H: 6.14; N: 1.70.

Specific rotation: $[\alpha]_D^{20}$ +137° (c 0.27, $H_2O$).

EXAMPLE 13

In a manner similar to Example 12 (1), 3.3 g of L-phenylalanine was treated for reaction to obtain 3.3 g (Yield 55%) of N-{(2-chloroethyl)-nitrosocarbamoyl}-L-phenylalanine as a yellow oil.

Specific rotation: $[\alpha]_D^{20}$ −30.5° (c 1.1, MeOH).

EXAMPLE 14

(1) Dissolved in tetrahyrofuran were 6.6 g of t-butyoxycarbonyl-DL-threonine and 3.1 g of triethylamine, to which was added dropwise 3.3 g of ethyl chlorocarbonate at 0° C. After stirring for two hours, 3.1 g of 2-amino-1,3,4-thiadiazole was added, and stirred at room temperature for further 20 hours. The reaction solution was concentrated under a reduced pressure, water was added to the residue, and the precipitates were collected by filtration to obtain 7.2 g (Yield 80%) of 2-(t-butoxycarbonyl-DL-threonyl)amino-1,3,4-thiadiazole as white crystals having a melting point of from 165° to 172° C. (dec.).

(2) Added to 6.0 g of the thus obtained amino-protected compound was 60 ml of a dioxane solution of hydrochloride (1.9 m mole/g). The mixture was reacted at room temperature for two hours. After the reaction, ether was added, and the resulting precipitates were collected by filtration to obtain 4.8 g (quantitative) of 2-DL-threonylamino-1,3,4-thiadiazole hydrochloride as white crystals having a melting point of 215° C. (dec.).

(3) Suspended in tetrahydrofuran was 3.6 g of the thus obtained hydrochloride, 2.1 g of triethylamine was added at 0° C. and then 2.1 g of N-2-chloroethylisocyanate was added dropwise. The mixture was stirred for two hours. The precipitates were removed by filtration and the filtrate was concentrated to obtain 4.5 g (Yield 73%) of 2-[N-{(2-chloroethyl)-carbamoyl}-DL-threonyl]amino-1,3,4-thiadiazole as white crystals having a melting point of from 192° to 196° C. (dec.).

(4) In a manner similar to Example 4(3), 3.1 g of 2-[N-{(2-chloroethyl)-carbamoyl}-DL-threonyl]amino-1,3,4-thiadiazole was treated for reaction to obtain 2.5 g (Yield 73%) of 2-[N-{(2-chloroethyl)-nitrosocarbamoyl}-DL-threonyl]amino-1,3,4-thiadiazole as slightly yellow prisms having a melting point of 130° C. (dec.).

Elementary analysis: Calculated for $C_9H_{13}N_6O_4SCl$ (%): C: 32.10; H: 3.89; N: 24.96; Found (%): C: 32.01; H: 3.93; N: 24.90.

EXAMPLE 15

(1) In a manner similar to Example 14(1), 10 g of t-butoxycarbonyl-L-tryptophane was treated for reaction to obtain 10.7 g (Yield 84%) of 2-(t-butoxycarbonyl-L-tryptophyl)amino-1,3,4-thiadiazole as white crystals having a melting point of from 98° to 101° C. (dec.).

Specific rotation: $[\alpha]_D^{20}$ +41.0° (c 1.2, MeOH).

(2) In a manner similar to Example 14(2), 7.5 g of the above condensation product was treated for reaction to obtain 6.3 g (quantitative) of 2-L-tryptophylamino-1,3,4-thiadiazole hydrochloride as slightly pink crystals having a melting point of from 204° to 209° C. (dec.).

Specific rotation: $[\alpha]_D^{20}$ +93.0° (c 1, MeOH).

(3) Suspended in 50 ml of tetrahydrofuran was 3.4 g of the above hydrochloride, added thereto at 0° C. was 1.1 g of triethylamine, and then 1.9 g of N-(2-chloroethyl)-N-nitrosocarbamoylazide was added thereto, and stirred at room temperature for 20 hours. The resulting precipitates were removed by filtration, and the crude crystals obtained from the filtrate were recrystallized from ethanol, to obtain 2.8 g (Yield 63%) of 2-[N-{(2-chloroethyl)-nitrosocarbamoyl}-L-tryptophyl]amino-1,3,4-thiadiazole as slightly yellow prisms having a melting point of 122° C. (dec.).

Elementary analysis: Calculated for $C_{16}H_{16}N_7O_3SCl$ (%): C: 45.55; H: 3.82; N: 23.24; Found (%): C: 45.76; H: 3.85; N: 23.19.

Specific rotation: $[\alpha]_D^{20}$ +1.7 (c 0.3, MeOH).

What is claimed is:

1. A nitrosourea derivative represented by the formula,

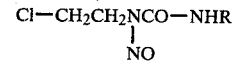

wherein —NHR represents a 2-(1,3,4-thiadiazolyl)amino group; an amino residue of a neutral α-amino acid, or an amino residue of a neutral α-amino acid whoe carboxyl group is amidated with 2-(1,3,4-thiadiazolyl)amine, or a pharmaceutically acceptable acid addition salt thereof.

2. The nitrosourea derivative as claimed in claim 1, which is represented by the formula,

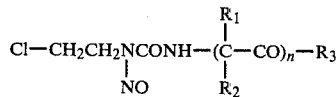

wherein $R_1$ and $R_2$ each represents a hydrogen atom, or a linear or branched lower alkyl, indolylalkyl, hydroxyalkyl, loweralkyl-thioalkyl, aryl or aralkyl group, or $R_1$ and $R_2$ combine together to form an alkylene group, n represents 0 or 1, with the proviso that when n is 0, $R_3$ represents a 1,3,4-thiadiazol-2yl group and when n is 1, $R_3$ is a hydroxyl group or a 2-(1,3,4-thiadiazolyl)-amino group, or pharmaceutically acceptable acid addition salts thereof.

* * * * *